United States Patent [19]

Martin

[11] Patent Number: 5,693,060
[45] Date of Patent: Dec. 2, 1997

[54] SUTURE SECURING DEVICE AND METHOD

[75] Inventor: Christopher Martin, Guildford, Australia

[73] Assignee: Smith & Nephew, Inc., Andover, Mass.

[21] Appl. No.: 479,240

[22] Filed: Jun. 7, 1995

Related U.S. Application Data

[63] Continuation of Ser. No. 97,691, Jul. 27, 1993, abandoned.

[30] Foreign Application Priority Data

Nov. 17, 1992 [AU] Australia .................... PL5843

[51] Int. Cl.⁶ .................................................. A61B 17/04
[52] U.S. Cl. ..................................................... 606/148
[58] Field of Search ................................. 606/148, 232, 606/151, 113, 139; 24/115 H, 115 G, 136, 129 D

[56] References Cited

U.S. PATENT DOCUMENTS

| | | | |
|---|---|---|---|
| 2,679,709 | 6/1954 | DuBois | 24/115 H |
| 3,080,867 | 3/1963 | Eichinger | 606/113 |
| 3,409,014 | 11/1968 | Shannon | 128/326 |
| 3,541,591 | 11/1970 | Hoegerman | 128/335 |
| 3,664,345 | 5/1972 | Dabbs et al. | 128/335 |
| 3,802,438 | 4/1974 | Wolvek | 128/335 |
| 3,880,166 | 4/1975 | Fogarty | 128/325 |
| 3,910,281 | 10/1975 | Kletscjka et al. | 128/335 |
| 3,976,079 | 8/1976 | Samuels et al. | 128/335 |
| 3,985,138 | 10/1976 | Jarvik | 128/326 |
| 4,235,238 | 11/1980 | Ogiu et al. | 128/334 R |
| 4,291,698 | 9/1981 | Fuchs et al. | 128/335 |
| 4,342,557 | 8/1982 | Bandar | 289/1.5 |
| 4,409,974 | 10/1983 | Freeland | 128/92 B |
| 4,741,330 | 5/1988 | Hayhurst | 128/92 YF |
| 4,750,492 | 6/1988 | Jacobs | 128/335 |
| 4,823,794 | 4/1989 | Pierce | 128/335 |
| 4,865,032 | 9/1989 | Jones | 128/340 |
| 4,918,785 | 4/1990 | Spinner | 287/17 |
| 4,932,962 | 6/1990 | Yoon et al. | 606/224 |
| 5,021,059 | 6/1991 | Kensey et al. | 606/213 |
| 5,074,874 | 12/1991 | Yoon et al. | 606/224 |
| 5,078,731 | 1/1992 | Hayhurst | 606/232 |
| 5,144,961 | 9/1992 | Chen et al. | 128/898 |
| 5,160,339 | 11/1992 | Chen et al. | 606/158 |
| 5,171,251 | 12/1992 | Bregen et al. | 606/151 |
| 5,182,838 | 2/1993 | Stenner | 24/712.7 |
| 5,192,287 | 3/1993 | Fournier et al. | 606/139 |

FOREIGN PATENT DOCUMENTS 492 172 A1 11/1991 European Pat. Off. .
48211 11/1982 U.S.S.R. .................. 606/139

*Primary Examiner*—Michael Buiz
*Assistant Examiner*—Tina T. D. Pham
*Attorney, Agent, or Firm*—Fish & Richardson P.C.

[57] ABSTRACT

A suture securing device for intracorporeally securing a suture. The device includes a surgically implantable body having a tissue abutting side and a suture loop side, and a passage through the body having an opening adjacent the tissue abutting side and another opening adjacent the suture loop side. When a loop of suture is positioned through the passage from the tissue abutting side and emerges from the suture loop side and a free portion of suture is passed through the loop, the loop clamps upon the free portion when the loop is retracted back into the passage.

15 Claims, 2 Drawing Sheets

SUTURE SECURING DEVICE AND METHOD

This is a continuation of application Ser. No. 08/097,691 filed on Jul. 27, 1993 now abandoned.

The present invention relates generally to surgical devices, more particularly it relates to a novel suture securing device and method for tying sutures. It will be convenient to hereinafter refer to the suture securing device and method in relation to endoscopic surgery however it should be noted that the invention has a wider application.

The basic principles of surgery are incision, dissection, traction, counter-traction, ligation and suturing. These principles are well established and mastered in conventional "open" invasive surgical procedures where access to the surgical site is gained by incision through the patient's skin and body wall to expose the site. In recent times attention has been directed towards least invasive surgical procedures or non-invasive procedures such as endoscopy, which encompasses arthroscopy, laparoscopy, duodenoscopy, gastroscopy and the like, where access to the surgical site is gained by introducing surgical instruments down one or more portals and/or gastrointestinal tract from the mouth or anus and/or urinary tract via the urethra. Least invasive surgery, where possible, has many benefits over conventional invasive procedures such as reduced surgical trauma, lessened anaesthesia and shortened recovery times, leading to reduced hospital costs, greater patient comfort and earlier return to work.

Although some of the technology for laparoscopic surgery has been available for many years, the first laparoscopic cholecystectomy performed in 1987 has stimulated the interest of general surgeons in laparoscopic surgery. Many general surgeons have transferred the basic principles of surgery to laparoscopic and endoscopic surgery and have mastered with reasonable ease these principles with the exception of suturing. In endoscopic procedures difficulty arises in tying of a suture as the surgeon can only use instruments to manipulate the required knots. Manipulation of the suture is hindered as usually the surgeon has only a two dimensional viewing field—the suture site being visible by use of a camera and television screen or specialized scope. The problem of suturing and especially tying knots during laparoscopic surgery has become more apparent as surgeons have moved from resectional surgery i.e. where part of an organ or tissue is completely or partially removed such as cholecystectomy or appendectomy, to surgery which requires suture placement such as procedures of fundoplication, bowel resection etc. Resectional procedures such as cholecystectomy and appendectomy generally only require ligature or clip application to tie off the removed organ or blood vessel. Devices have been developed to facilitate intracorporeal placement of such clips or ligatures and the application of such ligatures or clips is relatively simple when compared to tying of intracorporeal knots in sutures. At the present time the average surgeon is not confronted with the need for intracorporeal knot tying frequently enough to become adept at this skill and this may contribute to longer operating times. Considerable time and practice may be required before a surgeon becomes skilled at tying of knots during endoscopic surgery.

A method for tying knots extracorporeally has been developed where the slip knot is tied in the suture outside the body of the patient and then positioned at the desired site by means of a push-rod into the body. While this method is successful to some extent it suffers from a number of disadvantages. Many endoscopic procedures involve the inflation of a body cavity with a pressurized gas such as carbon dioxide so that a space is created in the body to make the surgical site visible. The gas pressure is kept constant to maintain the visual field and if the pressure is reduced by the escape of gas the visual field is lost or impaired as the body tissues resume their usual positions. In tying a knot in a suture outside the body it is necessary to pass the knot beyond a seal established to create the internal gas space. This involves breaking of the gas seal and the temporary loss of the gas space and hence the visual field as gas escapes when the suture is being passed into the body.

Secondly, the extracorporeally tied knots are not always as secure as would be desirable and thus present the risk of failure.

Thirdly, extracorporeally tied knots are not always satisfactory for securing opposite ends of a suture which closes an elongate wound.

Accordingly, it is an object of the present invention to provide a suture securing device particularly useful in endoscopic surgery which overcomes the abovementioned disadvantages of the prior art.

Another object of the invention is to provide a method for securing a suture which can be performed intracorporeally.

Yet another object of the invention is to provide a device which can be permanently implanted in the body of a patient to secure a suture.

Still another object of the invention is to provide a device which can be used to form secure ligature around a desired site.

Another object of the invention is to provide device which permits a suture adjusted to a desired position and secured.

Yet another aspect of the invention is to provide a method of suturing tissue to tissue or prosthesis to tissue intracorporeally using a device to secure one or both ends of the suture.

Other objects and advantages of the invention will become apparent from the following description.

In one aspect of the present invention there is provided a suture securing device for intracorporeally securing a suture comprising;

a surgically implantable body having a tissue abutting side and a suture loop side; and a passage through said body, said passage having an opening adjacent said tissue abutting side and another opening adjacent the suture loop side; and such that when a loop of suture is positioned through the passage from the tissue abutting side and emerging from the suture loop side and a free portion of suture is passed through said loop, said loop clamps upon the free portion when said loop is retracted back into said passage.

In preferred embodiment, the passage is configured such that a suture, looped through the passage of device and having a free end passed about the periphery of the device and through the loop, can be drawn from the tissue abutting side to the suture loop side but not from the suture loop side to the tissue abutting side. Generally the passage will accommodate two portions of a suture side by side but will not accommodate four portions of suture. Therefore if loop of suture which emerges from the passage on the suture loop side has a length of suture passed through the loop, the loop will clamp upon that length of suture if the loop is retracted back into the passage. Preferably the dimensions of the passage in transverse cross-section are such that it has a height equal to the diameter of a selected suture and a width two times the diameter of that suture.

At one or both ends of the passage the openings may be enlarged to positively seat the loop therein. Preferably there is a tapered recess at least about the opening adjacent the suture loop portion. There may also be provided a suture accommodating channel in the outside peripheral surface of the device. The channel is configured such that when said body is gripped about a portion of said outer peripheral surface, a portion of suture passing about said outer surface between said passage openings and located in said channel is not also gripped. The channel may be adapted to receive all or part of the suture which passes about the periphery of the device when the suture is appropriately positioned. Preferably the channel is provided such that when the suture securing device has a suture positioned about it, the device can be manipulated by a clamp which grips the periphery of the body but the suture passing in the channel is still able to slide freely underneath the clamp so that the device can be positioned accordingly. Preferably the channel is parallel to the passage.

The device may also include locating portions to cooperatively engage with an apparatus for positioning the device. A suitable apparatus for positioning the device is described in co-pending Australian application PL 5989. Locating portions may be recesses at either end of the device adapted to engage corresponding holding members on a suitable positioning apparatus such that the device is held securely in the positioning apparatus until intentionally dislodged from the holding members thereof.

The body of the device may be elongate and may have a central axis. The suture passage may be a transverse passage which bisects the central axis.

In another aspect of the invention, the device may be provided with a second suture passage therethrough positioned along the axis of the device from the first passage and preferably substantially parallel to the first passage. In one embodiment of this aspect of the invention, the diameter of the second bore is preferably only marginally larger than the diameter of the selected suture so that a knot in a suture will not pass through the passage.

In another embodiment of this aspect of the invention the second suture passage may be of the same dimensions and/or have the same functional features as the first suture passage. In this embodiment the suture securing device may be utilized to secure two separate sutures or alternatively both ends of one suture so as to form a ligature. The two passages may be of different dimensions such that two different types of suture may be secured. In this embodiment where two passages are provided the channel may be configured so that it accommodates portions of both sutures secured.

In another aspect of the invention there is provided a method for securing a suture comprising:

(a) providing a suture securing device comprising a body having a tissue abutting side and a suture loop side and a passage through said body, the passage having an opening adjacent the tissue abutting side and another opening adjacent the suture loop side;

(b) passing a loop of said suture to be secured through said opening from said tissue abutting side to said suture loop side;

(c) passing a free end of said suture about said device and through said loop;

(d) drawing taut the portion of suture passed through said loop; and (e) pushing said device along said suture to a desired position.

It will now be convenient to describe the invention in more detail with reference to a preferred embodiment illustrated in the accompanying drawings. It is to be understood that the drawings and the following description relate to a preferred embodiment only, and not intended to limit the scope of the present invention.

Figure 1:
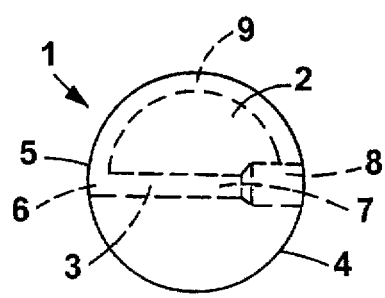
FIG. 1 is an end elevation of a suture securing device made in accordance with one embodiment of the present invention.
Figure 2:
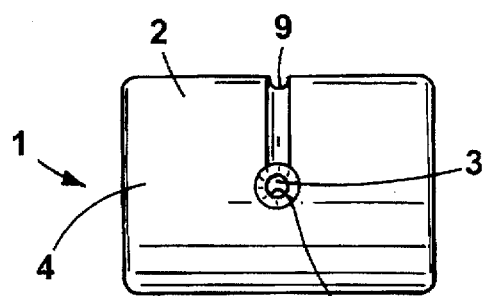
FIG. 2 is a side elevation of a suture securing device of FIG. 1.

Suture securing device 1 comprises a body 2 having a suture passage 3 therethrough. Device 1 may be any suitably shape such as a cylinder, sphere, cube, rectangular prism or the like but preferably the device is a rectangular prism. When the device is a rectangular prism preferably the external edges of the prism are radiussed in order to prevent abrasion of the suture when connected to the device and to prevent damage to surrounding body tissues once the device is implanted.

Body 2 has a tissue abutting side 5 which is suitably to bear against a body tissue when a suture is secured by device 1. Body 2 also has a suture loop side 4. Suture loop portion 4 may be on the opposite side of body 2 to tissue abutting side 5. Suture passage 3 passes through body 2 and has openings 6 and 7 adjacent tissue abutting side 5 and suture loop side 4 respectively. At opening 7 adjacent suture loop side 4 there may be provided a tapered recess 8 adapted to seat a knot in the suture.

Suture accommodating channel 9 may be provided in the outside wall of body 2. Suture accommodating channel 9 passes between openings 6 and 7. Two suture accommodating channels (not shown) may be provided, one passing over the top of body 2 between opening 6 and 7 and another channel passing below body 2 between opening 6 and 7. Preferably, suture accommodating channel 9 is configured such that when a suture is located in said channel 9 and device 1 is held in a surgical clamp about the region of channel 9, the suture is still able to freely pass beneath the clamp, i.e. the suture is not also held by the clamp when the body is clamped.

Figure 3:
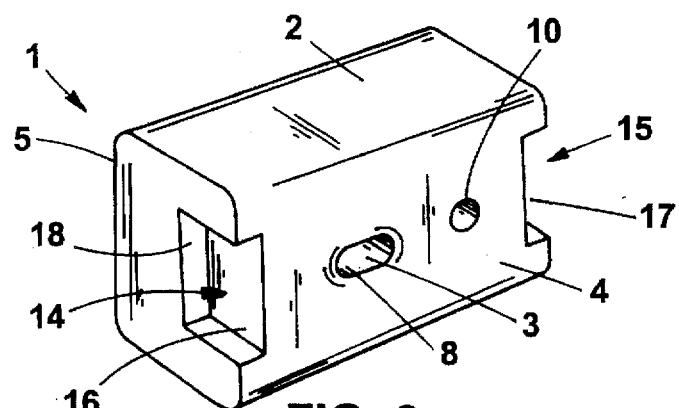
FIG. 3 is a perspective view of a suture securing device made in accordance with another aspect of the invention.
Figure 4:
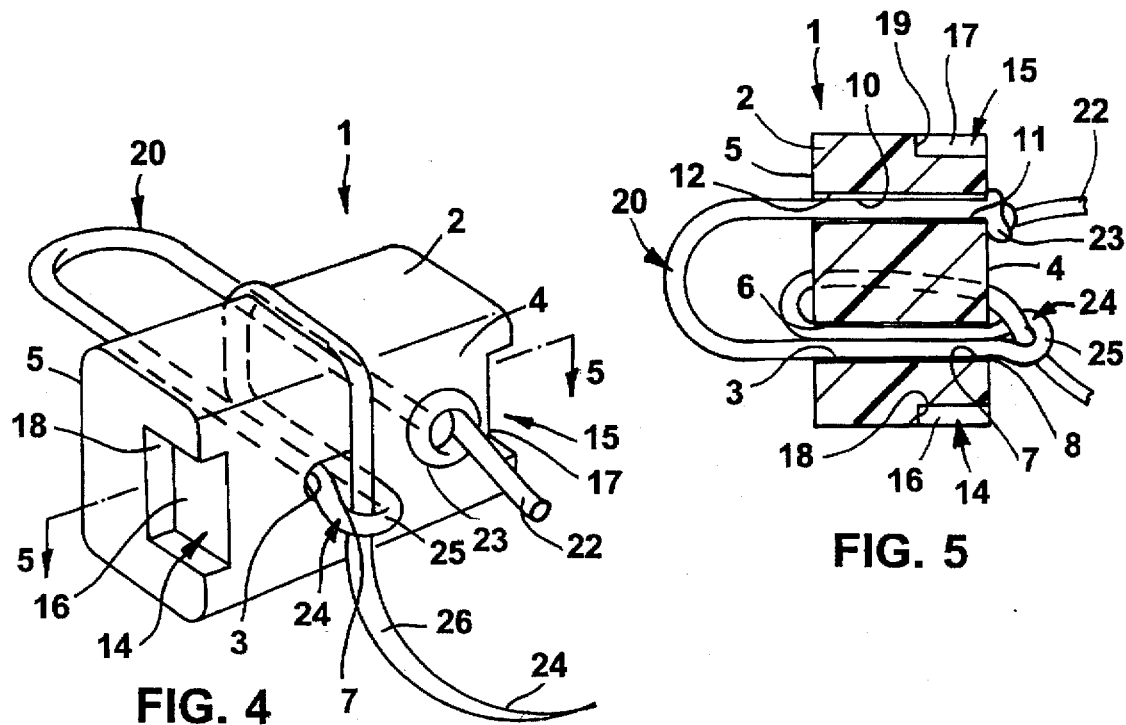
FIG. 4 is a transparent perspective view of a suture securing device of FIG. 3 shown with a suture in place.
Figure 5:
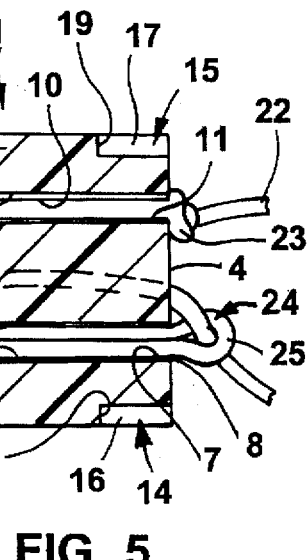
FIG. 5 is a transverse section of the device of FIG. 4.

Preferably, suture passage 3 is configured so that a loop of suture emerging from the passage and which has a portion of suture passed therethrough will clamp upon the portion of suture if the loop is retracted back into the passage. In another embodiment of the invention, there is also provided a second suture passage 10 which passes between tissue abutting portion 5 and suture loop portion 4 and has openings 11 and 12 adjacent portions 5 and 4. In FIG. 3, second suture passage 10 is adapted to accommodate only one portion of a suture at any one time i.e. the diameter of second suture passage 10 is approximately equal to the diameter of a selected suture. Opening 11 may be provided with a knot locating recess (not shown) adapted to locate a knot tied in a suture which is passed through second suture passage 10.

Body 2 is further provided with locating portions 14 and 15 adapted to co-operate with corresponding holding members on an applicator apparatus suitable for use with device 1. Locating portions 14 and 15 may be recesses 16 and 17 at opposite ends of device 1. Recesses 16 and 17 may include walls 18 and 19 which are adapted to be pressed upon by holding members on the applicator apparatus.

Device 1 can be used to secure a suture for a variety of surgical procedures. In one embodiment a single device according to the invention can be used to form a secure loop such as for ligation or the like. In this embodiment a suture 20 is selected, preferably with surgical needle 21 attached. Suture 20 and surgical needle 21 may be any suitable suture and surgical needle known in the art. For example suture 20 may be any selected size of catgut, chromic or plain suture or synthetic or absorbable or non-absorbable or monofilament or braided suture or the like. Distal end 22 of suture 20 is first passed through second suture passage 10 and a knot 23 is tied in distal end 20 on the suture loop side of body 2. Knot 23 may then be drawn towards knot locating recess (not shown) and seated therein. When the diameter of second suture passage 10 will only accommodate a single portion of suture 20 knot 23 cannot be drawn through passage 10. Suture 20 may then be used to snare or ligate tissue, tubes or vessels or suture tissue or prostheses. To secure the proximal needle 21 end of suture 20 a loop 24 of suture 20 is drawn through suture passage 3 from the tissue abutting side 5 of body 2 until the head 25 of loop 24 projects beyond opening 7. Loop 24 may be drawn through suture passage 3 by any suitable means. Loop 24 may be drawn through passage 3 by a threading means such as a loop of fine wire or suture material or the like which can be passed through suture passage 3 from the suture loop side to the tissue abutting side until the head of the loop of the threading means extends out of opening 6. Surgical needle 21 and proximal end 26 of suture 20 can be passed through the head of the threading means and the threading means then retracted through passage 3 to draw the proximal end of suture 20 therethrough. Threading means can then be disengaged from head 25. Suture needle 21 can then be threaded through head 25 and suture 20 drawn therethrough. Where suture accommodating channel 9 is provided the portion of suture 20 overlying body 2 between opening 6 and 7 may locate in channel 9. Device 1 may then be positioned at the desired surgical site. Needle 21 or the portion of suture 20 between needle 21 and that passing through head 25 is held securely by a grasping means and the suture is drawn taut. Device 1 can then be manoeuvred to the desired surgical site. Pushing means may be provided preferably with tines which engage in locating portions 14 and 15. Device 1 can then be pushed along suture 20 to a site where the tissue abutting side 5 comes into contact with the sutured body tissue. Device 1 and suture 20 co-operate such that the device cannot then move towards the suture needle 21. Tension on the ligating or suturing portion of suture 20 acts to draw loop head 25 back through passage 3. Head 25 thus clamps upon the portion of the suture which passes through head 25. As suture passage 3 cannot accommodate four thicknesses of the suture, the portion of the suture passing through head 25 will not fit through passage 3. As long as there is some tension on the suture in the ligating or suturing region, that tension will be applied as a clamping force on the portion of the suture passing through head 25. Once in position, device 1 will not readily move from its position. The needle end of suture 20 may be severed as desired and the needle and severed suture removed from the operating site.

In another embodiment of the invention, two devices in accordance with the invention may be used to secure a suture along an elongate wound. A first device is attached to the distal end of a suture. The first device need not include a second suture passage. A portion of the distal end of a suture is drawn through suture passage 5 until a loop head 25 projects beyond body 2. The distal end of the suture is then threaded through the head of 25 of the loop. Suturing can then commence and the suture drawn through the body tissue until the tissue abutting portion 5 comes into contact with the body tissue. The distal end of the suture can not be drawn through the body tissue. Suturing can continue along the elongate wound away from the first device.

After the wound has been completely closed the procedure for attaching a second suture securing device can be performed about the proximal end of the suture i.e. by drawing a loop of suture through suture passage 3, passing the needle and adjacent suture through the head of the loop, drawing the suture between the needle and loop head taut and pushing the device along the suture towards the body tissue until the device comes into contact with and is secure against the body tissue. The suture is then severed and the needle and severed suture removed from the operating site.

Figure 6:
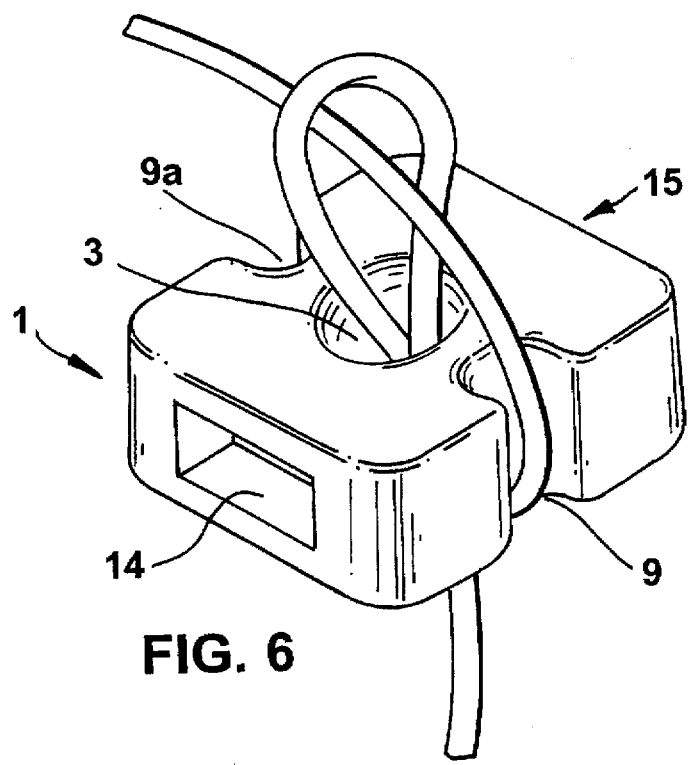
FIG. 6 is a perspective view of a suture securing device made in accordance with another aspect of the invention with a suture in place.

In FIG. 6 device 1 has a single passage 3 therethrough. Device 1 has two channels 9 and 9a in its outside wall. Channels 9 and 9a are substantially parallel to passage 3.

Device 1 has locating recesses 14 and 15 (not shown) adapted to locate corresponding holding members on an apparatus for positioning the device.

Figure 7:
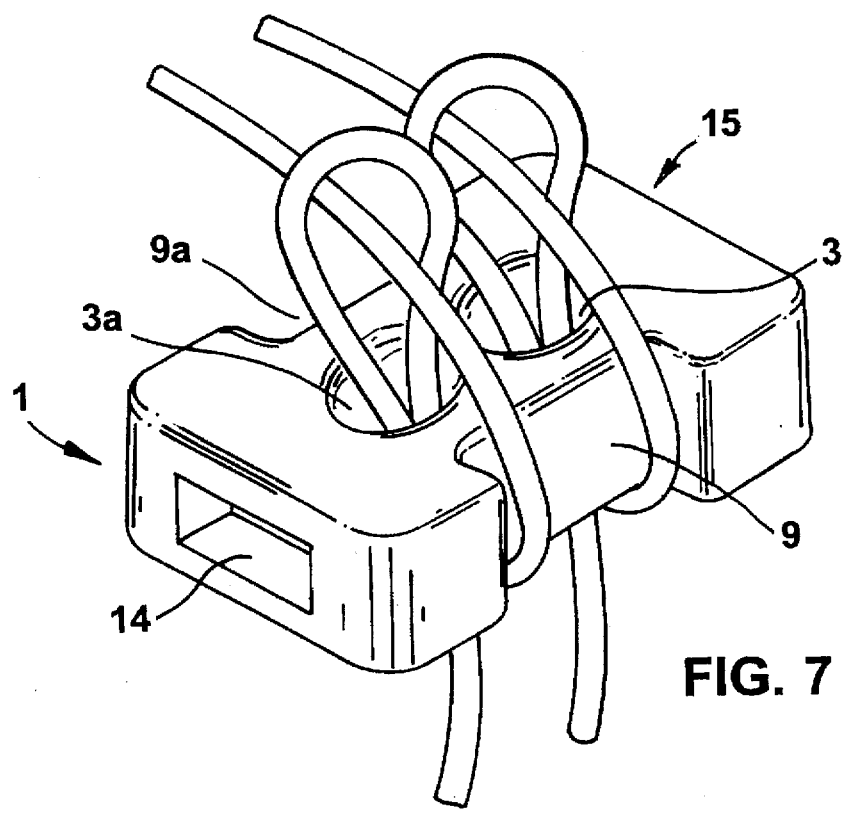
FIG. 7 is a perspective view of a suture securing device made in accordance with yet another aspect of the invention with two sutures in place.

In FIG. 7 device 1 has a pair of passages 3 and 3a adapted to secure two sutures or two ends of one suture. Device 1 has channels 9 and 9a in its outside wall which accommodate portions of both sutures being secured.

It will be readily apparent that a plurality of suture securing devices may be used during a surgical procedure. As different strengths and thicknesses of suture may be used by a surgeon it will be appreciated that a range of suture securing devices may be provided with different sized suture passages appropriate for corresponding suture sizes. The suture securing device may be any suitable size according to the desired application. The suture securing device may be made from any suitable material which is acceptable for implantation into the body of a patient. The device may be made from a non-absorbably polymeric material, for example high density polyethylene or a plastic sold under the trade mark DELRIN. The device may be made from a bio-absorbable material which is known in the art such as polyglycolic acid.

The device may be manufactured by any suitable method known in the art. The device may be made by injection moulding. The device may be made under aseptic conditions and packages in a sterile form immediately after manufacture or may be manufactured under non-sterile conditions and subsequently sterilized by any suitable means.

It is to be understood that various modifications, additions and/or alterations may be made to the parts previously described without departing from the ambit of the present invention.

I claim:

1. A suture securing method comprising:
   (a) providing a suture;
   (b) providing a suture securing device that includes a body having a tissue abutting side, a suture loop side, and a passage having a selected diameter extending therebetween, said passage having open ends at said tissue abutting side and at said suture loop side;
   (c) passing a loop of suture through said passage from said open end at said tissue abutting side through said open end at said suture loop side;
   (d) passing a free end of said suture about said body and through said loop, and drawing taut the free end of the suture that has been passed through said loop;

(e) pushing said body along the suture away from the free end to a desired position, said selected diameter of said passage being sufficient to allow the suture to slide in said passage as said body moves along the suture to said desired position; and (f) applying tension to the suture when said body is in said desired position to retract a portion of said loop and the portion of the suture which passes through said loop into said passage, thereby to clamp said portion of the suture within said passage.

2. The method of claim 1 wherein said body has an outer peripheral surface that includes a suture accommodating channel having a depth and a width greater than a thickness of the suture so that the suture is recessed with respect to said outer peripheral surface when placed in said channel and can freely move within said channel during said pushing step.

3. The method of claim 1 wherein at least said open end at said tissue abutting side is enlarged with respect to said selected diameter to receive the retracted portion of said loop and the portion of the suture that passes through the loop.

4. Apparatus comprising:

a suture;

a suture securing device that includes a surgically implantable body having a tissue abutting side, a suture loop side, and a passage having a selected diameter disposed through said body, said passage having open ends at said tissue abutting side and at said suture loop side, said open end at said suture loop side being enlarged with respect to said selected diameter;

the suture having two ends and a loop therebetween, the suture passing from said tissue abutting side, through said passage to said suture loop side and back through said passage to said tissue abutting side such that the loop emerges from said open end of said passage at said suture loop side, and a first one of said ends passing about said body and through said loop;

said selected diameter of said passage being sufficient to allow said body to be pushed along the suture away from said first end to a desired position with respect to a second one of said ends, with the suture sliding in said passage as said body moves along the suture to said desired position.

5. The apparatus of claim 4 wherein said body has an outer peripheral surface that includes a suture accommodating channel having a depth and a width greater than a thickness of the suture so that the suture is recessed with respect to said outer peripheral surface when placed in said channel and can freely move within said channel during said pushing step.

6. The apparatus of claim 5 wherein said channel extends substantially parallel to said passage.

7. The apparatus according to claim 4 wherein said enlarged open end comprises a counter-bore of said passage.

8. The apparatus according to claim 4 wherein one of said free ends of said suture has a suturing needle connected therewith.

9. Apparatus for intracorporeally securing a suture, comprising:

a suture;

a surgically implantable body having a tissue abutting side, a suture loop side, and a passage extending therebetween, said passage having open ends at said tissue abutting side and at said suture loop side, at least said open end at said suture loop side being enlarged with respect to a diameter of said passage;

the suture having two ends and a loop therebetween, the suture passing from said tissue abutting side, through said passage to said tissue abutting side such that the loop emerges from said enlarged open end of said passage on said suture loop side, and a first one of said ends passing about said body and through said loop;

said diameter of said passage being sufficient to allow said body to be pushed along the suture away from said first end to a desired position with respect to a second one of said ends, with the suture sliding in said passage as said body moves along the suture to said desired position; and said enlarged open end of said passage being configured to allow a portion of said loop and the portion of the suture which passes through said loop to be retraced through said enlarged open end into said passage.

10. The apparatus of claim 9 wherein said body has an outer peripheral surface that includes a channel positioned to receive a portion of a free end of the suture that is passed about said body and through said loop, said channel having a depth and a width greater than a thickness of the suture so that said portion of the suture is recessed with respect to said outer peripheral surface and can freely move within said channel, thereby to allow said body to be gripped at said outer peripheral surface and pushed along the suture.

11. The apparatus according to claim 10 wherein said channel extends substantially parallel to said passage.

12. The apparatus according to claim 10 wherein said outer peripheral surface includes locating portions thereon to provide surfaces adapted to be gripped to push the body along the suture to the desired position.

13. The apparatus according to claim 12 wherein said body is substantially rectangular in shape having two side walls longer in length than two end walls, and said locating portions include a recess at each end wall of the implantable body between the tissue abutting side and the suture loop side.

14. The apparatus according to claim 9 wherein external surfaces of said body are radiussed.

15. The apparatus according to claim 9 wherein said loop is drawable from the tissue abutting side to the suture loop side but not from the suture loop side to the tissue abutting side.

* * * * *